United States Patent [19]

Kazem-Goudarzi et al.

[11] Patent Number: 5,108,024
[45] Date of Patent: Apr. 28, 1992

[54] METHOD OF INSPECTING SOLDER JOINTS

[75] Inventors: Vahid Kazem-Goudarzi, Sunrise; Edward J. Hall, Miami; Kiron P. Gore, Coral Springs, all of Fla.

[73] Assignee: Motorola, Inc., Schaumburg, Ill.

[21] Appl. No.: 709,248

[22] Filed: Jun. 3, 1991

[51] Int. Cl.$^5$ .............................................. B23K 1/00
[52] U.S. Cl. ................................. 228/104; 228/56.5; 29/593; 118/713
[58] Field of Search ............... 228/103, 104, 180.2, 228/56.5; 29/593; 427/96, 64; 118/712, 713; 156/64

[56] References Cited

U.S. PATENT DOCUMENTS 4,944,447 7/1990 Thome ............................ 228/104

FOREIGN PATENT DOCUMENTS 2937077 3/1981 Fed. Rep. of Germany ........ 29/593
56-82544 7/1981 Japan ................................. 29/593

OTHER PUBLICATIONS

IBM Technical Disclosure Bulletin, "Micromanipulator Liquid Contact Tester Probe", vol. 15, No. 1, p. 344, Jun. 1972.
IBM Technical Disclosure, Inspection Technique for Solder Reflow Pad Height/Volume, by T. Ross and A. Townsend, vol. 22, No. 9 Feb. 1980.

Primary Examiner—Samuel M. Heinrich
Attorney, Agent, or Firm—Pablo Meles

[57] ABSTRACT

A solder joint inspection system comprises a substrate (60) having at least one solder pad (56), a predetermined amount of solder (54) on the solder pad, and an image fluxing material (52) that fluoresces when an ultraviolet light source (42) is applied to the solder (54) and the fluxing material (52). When an ultraviolet light source is applied to the substrate having a predetermined amount of solder and fluxing material, a visual inspecting device (40) can verify if, in fact, the predetermined amount of solder and fluxing material is present.

22 Claims, 4 Drawing Sheets

METHOD OF INSPECTING SOLDER JOINTS

TECHNICAL FIELD

This invention relates to vision inspection of solder joints on printed circuit boards and chip carriers, and more particularly to a method of detecting defective solder joints by using flux and ultraviolet light.

BACKGROUND OF THE INVENTION

Inspection of solder ball or solder joints is crucial in achieving high quality non-defective circuit boards. In particular, with the trend towards the use of surface mounted components, the importance of determining whether an effective amount of solder and flux is applied to the solder joint before the components are mounted becomes even more critical. To avoid an unacceptable yield and having to rework or scrap the printed circuit board, the soldering process is periodically monitored by visual inspection. If an insufficient amount of solder or flux exists, the likelihood of circuit board (or module) failure becomes certain. Thus, existing vision systems attempt to determine whether an effective amount of solder and/or flux exists. Unfortunately, to the human eye, the conventional inspections of solder joints in two-dimensions may provide a false conclusion as to the effectiveness of the solder joint or flux or even the existence of the solder joint itself. Furthermore, to the human eye, flux appears clear when applied to a printed circuit board. Thereby providing further room for error during visual inspection.

When conventional vision inspection systems use white light (incandescent or fluorescent) to inspect a joint, the two dimensional view of a solder joint having an insufficient amount of solder or flux may still appear as if it were sufficient. Thus, present vision schemes are ineffective in accurately determining the efficacy of a solder joint. Other vision systems may use dyes to enhance the inspection when using white light. Unfortunately, the dye may cause dendritic growth or corrosion in the solder joint.

Having an appropriate amount of flux on the under side of an integrated circuit (as in the C-5 Process for Chip Carriers) is required to act as an activator during reflow and to provide a tacking media during transportation. Too much flux causes the integrated circuit to float away when the flux liquifies. An insufficient amount of flux fails to provide enough tackiness during transportation. A need exists for a method to accurately determine the effectiveness of a solder joint and the added flux before surface mounted components are mounted that does not necessarily require additional production steps.

SUMMARY OF THE INVENTION

A solder joint inspection system comprises a substrate having at least one solder pad, a predetermined amount of solder on the solder pad, and an image fluxing material that fluoresces when an ultraviolet light is applied to the solder and the image fluxing material. When an ultraviolet light source is applied to the substrate having a predetermined amount of solder and fluxing material, a visual inspecting device can verify if, in fact, the predetermined amount of solder and fluxing material is present.

DESCRIPTION OF THE PREFERRED EMBODIMENT

Figure 1:
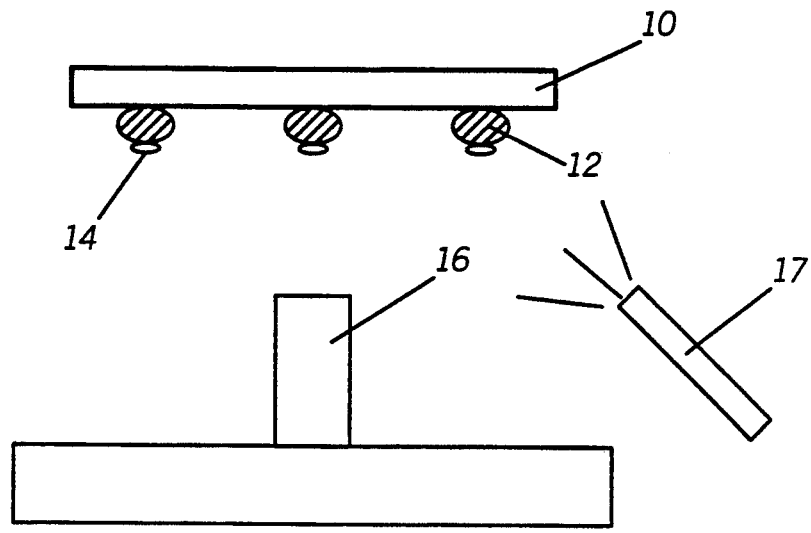
FIG. 1 is a side view of a solder joint vision inspection system in accordance with the present invention having an effective amount of solder and flux.
Figure 2:
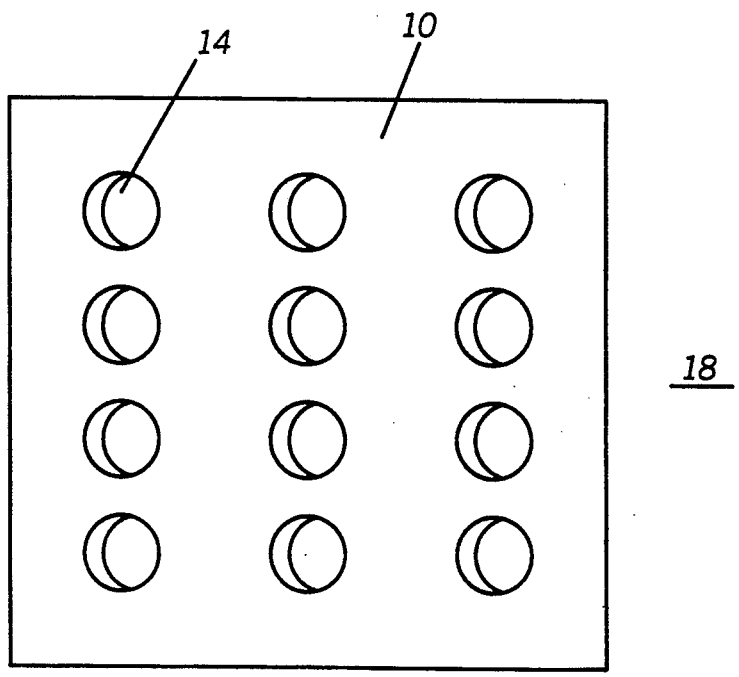
FIG. 2 is a bottom plan view of an array of solder joints of FIG. 1 as seen by the vision system camera in accordance with the present invention.

Referring to FIG. 1, there is shown a vision inspection system 100 in accordance with the present invention for detecting inadequate amounts of flux and defective solder joints. The vision inspection system 100 preferably comprises of a vision inspecting means 16 such as a digital scanning camera or the like. The vision inspecting means 16 could typically inspect the efficacy of the solder bumps on a solder bumped component such as a chip carrier or semiconductor die preferably comprising of a substrate 10, a predetermined sized of solder bumps 12, and an predetermined effective amount of flux 14 which also serves as a tacking agent. When an ultraviolet light source 17 is applied to the underside of the solder bumped component (the solder bumps), the flux on the solder bump fluoresces. For example, if the substrate 10 has an array of 3 by 4 solder bumps (12) and there exists an appropriate amount of solder and flux (14), then a two dimensional image 18 or representation (bottom plan view) as seen by the vision inspecting means 16 would appear as in FIG. 2. The ultraviolet light causes the flux 14 to fluoresce, and thereby providing a image that stands out clearly. Other vision systems fail to reliably provide such an accurate image that proportionately portrays the amount of flux and solder in a fluoresced image as in the present invention.

Figure 3:
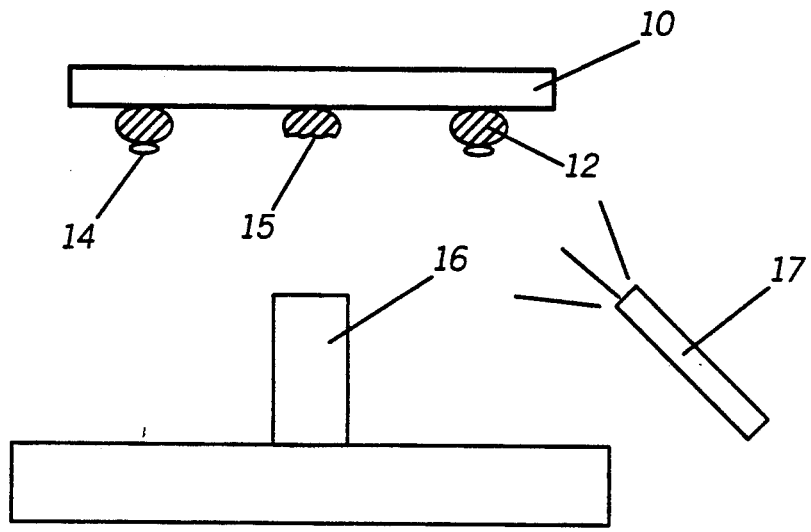
FIG. 3 is a side cut view of a solder joint vision inspection system in accordance with the present invention having an insufficient amount of solder and flux in one of the joints.
Figure 4:
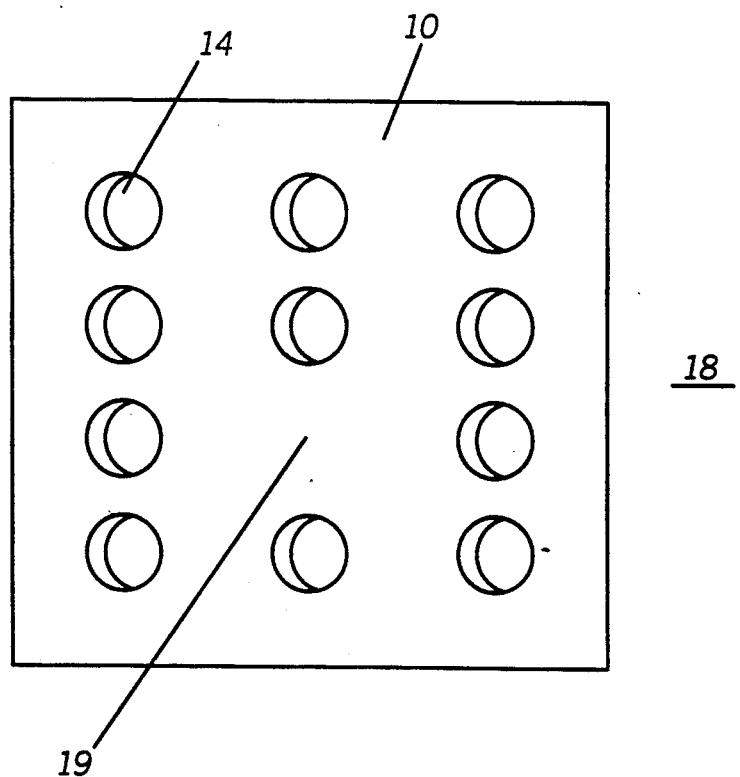
FIG. 4 is a bottom plan view of an array of solder joints of FIG. 3 as seen by the vision system camera in accordance with the present invention.

FIG. 3 shows the same vision inspection as in FIG. 1, except that the solder bumped component has an insufficient amount of solder 15. When flux 14 is applied and the solder bumped component is exposed to an ultraviolet light source 17, then a two-dimensional image 18 as shown in FIG. 4 would reveal the substrate 10 and fluorescent flux 14. Since an insufficient amount of solder (15) exists (and no flux exists on solder bump 15) in one of the solder bumps, the image 18 would also reveal a gap or void (19) that would represent a lack of flux or a lack of a solder ball. If some, but an insufficient amount of either solder and/or flux existed, then the image 18 would likely reveal a much smaller fluorescing image (not shown) of the flux 14 in the place of the void 19. Again, the image of the flux will be proportional to the actual amount of flux existing on the solder joint.

Figure 5A:
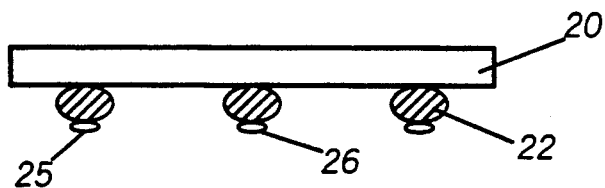
FIG. 5A is a side view of a fluxed solder bumped component, chip carrier or die in accordance with the present invention.
Figure 5B:
FIG. 5B is side view of a substrate having a plurality of solder pads.
Figure 5C:
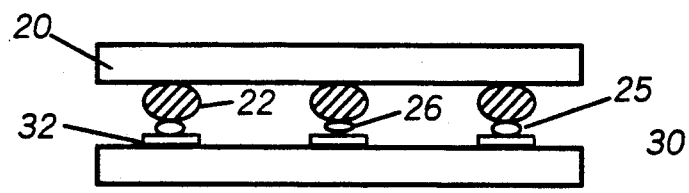
FIG. 5C is a side view of the solder bumped component being dipped upon the substrate and solder pads in accordance with the present invention.
Figure 5D:
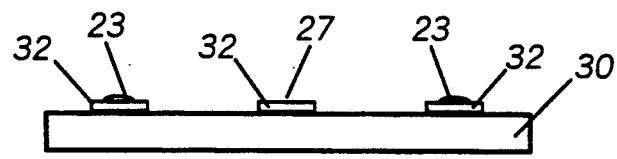
FIG. 5D is a side view of the substrate and solder pads of FIG. 5C after the fluxed solder bumped component is removed in accordance with the present invention.
Figure 5E:
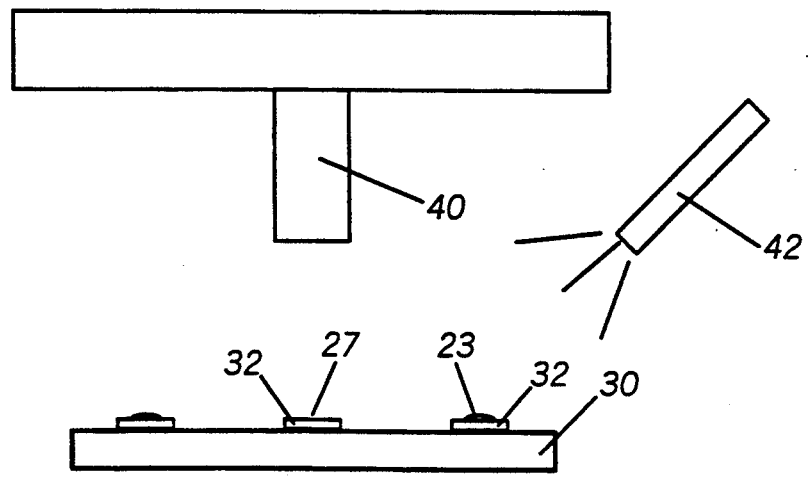
FIG. 5E is a side view of another solder joint vision inspection system in accordance with the present invention.

Referring to FIG. 5A–5C, there is shown another process of vision inspecting a solder bumped component in accordance with the present invention. As before a solder bumped component is provided preferably having a substrate 20, solder bumps 22, and flux 25. In this instance, the middle solder bump and flux 26 has an insufficient amount of either solder or flux. In this process, the fluxed solder bumped component is dipped on a substrate 30 having corresponding solder pads 32 as shown in FIG. 5B and 5C. Referring to FIG. 5D, once the solder bumped component is removed, a predetermined residual amount of flux 23 is left upon the solder pads 32 of the substrate 30, except where an insufficient amount of solder or flux resides (26). Thus, when the fluxed solder bumped component is dipped upon the substrate, only the areas having a sufficient amount of flux and solder will leave a residue (23). Otherwise, no residue will remain on the top surface (27) of the solder pad 32 as shown in FIG. 5D. Referring to FIG. 5E, an ultraviolet light source 42 fluoresces the residual flux 23 and allows a vision inspecting means 40 to visually inspect the efficacy of the solder bumps 22 and flux by taking an image of the substrate 30 and the flux 23 upon the solder pads 32. Preferably, the vision system compares the image with a stored image to determine if appropriate amounts of flux and solder exists. Otherwise, a human eye inspection could also serve the same purpose. If the flux fails to fluoresce where expected (27), then the user can repair the defective solder bumped component before it is mounted on a printed circuit board for a electronic device or either discard the defective component.

Figure 6:
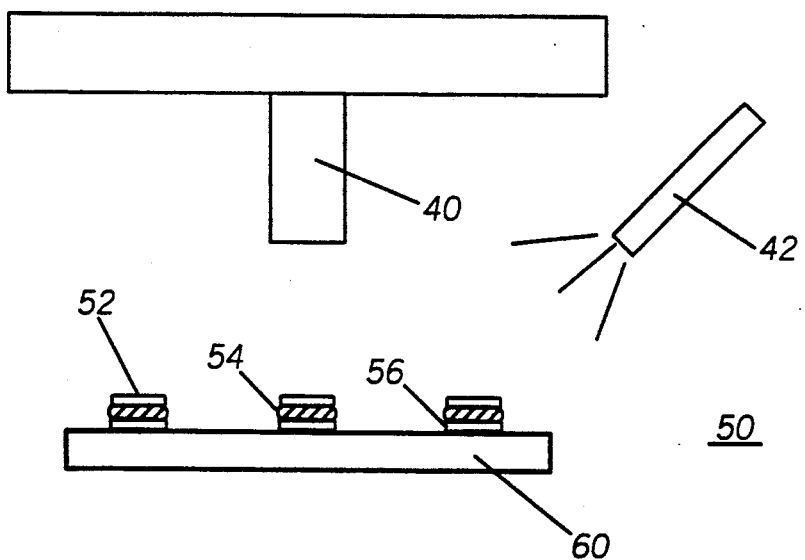
FIG. 6 is a side view of an alternative solder joint vision inspection system in accordance with the present invention where a solder cladded printed circuit board is inspected.

Referring to FIG. 6, there is shown a solder inspecting system for preferably inspecting a solder cladded printed circuit board 50. In other words, a printed circuit board having solder 54 either reflowed or electroplated on the solder pads 56 of the substrate 60 of the printed circuit board 50. As before, a flux 52 is applied to the solder joints and then an ultraviolet light source 42 is applied on the surface of the printed circuit board 50. The vision inspecting means 40, with the appropriate light filters (such as polarizing filters), again will be able to determined the efficacy and integrity of the solder joints and flux before surface mounted components are mounted on the printed circuit board 50.

We claim as our invention:

1. A method of inspecting a solder joint, comprising the steps of:
   providing a substrate having at least one solder pad;
   applying solder to said substrate on the solder pad;
   applying an image flux on the solder;
   applying an ultraviolet light on the substrate to detect whether a predetermined amount of solder volume resides on the solder pad;
   vision means for inspecting said substrate.

2. The method of claim 1, wherein applying said solder is done by screen printing.

3. The method of claim 1, wherein applying said solder is done by electroplating.

4. The method of claim 1, wherein the image flux also serves as a tacking media.

5. The method of claim 1, wherein the vision means for inspecting comprises of a human eye inspection.

6. The method of claim 1, wherein the vision means for inspecting comprises of a visual comparison inspection with a stored image.

7. A method of inspecting a solder joint, comprising the steps of:
   providing a solder bumped component;
   applying image flux on the solder bump;
   applying an ultraviolet light on the substrate to determined whether a predetermined amount of solder volume is attached to the solder bumped component;
   vision means for inspecting said solder bumped component.

8. The method of claim 7, wherein the solder bumped component is a chip carrier.

9. The method of claim 7, wherein the solder bumped component is a solder bumped semiconductor die.

10. The method of claim 7, wherein the image flux also serves as a tacking media.

11. The method of claim 7, wherein the vision means for inspecting comprises of a human eye inspection.

12. The method of claim 7, wherein the vision means for inspecting comprises of a visual comparison inspection with a stored image.

13. A method of inspecting a solder joint, comprising the steps of:
   providing a solder bumped component;
   providing a substrate having solder pads, at least some of said solder pads for receiving the solder bumps;
   applying image flux on the solder bump;
   dipping said image fluxed solder bumped component on some of the solder pads of the substrate to provide an image mask;
   applying an ultraviolet light on the substrate to determined whether a predetermined amount of solder volume is attached to the solder bumped component;
   vision means for inspecting said solder bumped component.

14. The method of claim 13, wherein the solder bumped component is a chip carrier.

15. The method of claim 13, wherein the solder bumped component is a solder bumped semiconductor die.

16. The method of claim 13, wherein the image flux also serves as a tacking media.

17. The method of claim 13, wherein the vision means for inspecting comprises of a human eye inspection.

18. The method of claim 13, wherein the vision means for inspecting comprises of a visual comparison inspection with a stored image.

19. A solder joint inspection system, comprising:
   a substrate having at least one solder pad;
   a predetermined amount of solder on said solder pad;
   image fluxing means for providing a flux that fluoresces when an ultraviolet light is applied to said solder and said image fluxing means;

an ultraviolet light source applied to the substrate having a predetermined amount of solder and image fluxing means;

a vision means for visually inspecting said predetermined amount of solder and said image fluxing means.

20. The solder joint inspection system of claim 19, wherein the vision means for inspecting comprises of a human eye inspection.

21. The solder joint inspection system of claim 19, wherein the vision means for inspecting comprises of a visual comparison inspection with a stored image.

22. The solder joint inspection system of claim 19, wherein the image fluxing means comprises any material that fluoresces when an ultraviolet light source is applied to the material.

* * * * *